United States Patent
Boulanger

(10) Patent No.: US 12,116,372 B1
(45) Date of Patent: Oct. 15, 2024

(54) PROCESS FOR PREPARING METHYL 3-BROMO-2-(2,3,4,9-TETRAHYDRO-1H-PYRIDO[3,4-B]INDOL-1-YL)PROPANOATE

(71) Applicant: William Allen Boulanger, Mahomet, IL (US)

(72) Inventor: William Allen Boulanger, Mahomet, IL (US)

(*) Notice: Subject to any disclaimer, the term of this patent is extended or adjusted under 35 U.S.C. 154(b) by 0 days.

(21) Appl. No.: 18/539,527

(22) Filed: Dec. 14, 2023

(51) Int. Cl.
| | |
|---|---|
| C07D 471/12 | (2006.01) |
| C07C 69/02 | (2006.01) |
| C07D 209/16 | (2006.01) |
| C07D 307/20 | (2006.01) |
| C07D 317/26 | (2006.01) |
| C07D 471/04 | (2006.01) |
| C07D 487/04 | (2006.01) |

(52) U.S. Cl.
CPC ............ C07D 487/04 (2013.01); C07C 69/02 (2013.01); C07D 209/16 (2013.01); C07D 307/20 (2013.01); C07D 317/26 (2013.01); C07D 471/04 (2013.01)

(58) Field of Classification Search
CPC .................................................. C07D 471/12
USPC .......................................................... 546/85
See application file for complete search history.

(56) References Cited

U.S. PATENT DOCUMENTS

| | | | |
|---|---|---|---|
| 3,478,051 A | 11/1969 | Houlihan et al. | |
| 3,525,750 A | 8/1970 | Renner | |
| 3,681,362 A | 8/1972 | Nagata et al. | |
| 4,122,082 A | 10/1978 | Wright et al. | |
| 4,146,643 A | 3/1979 | Pfaffli | |
| 4,154,943 A | 5/1979 | Kuehne | |
| 4,220,774 A | 9/1980 | Kuehne | |
| 4,267,330 A | 5/1981 | Kuehne | |
| 4,283,536 A | 8/1981 | Kuehne | |
| 4,362,739 A | 12/1982 | Kuehne | |
| 4,428,880 A | 1/1984 | Kuehne | |
| 4,490,378 A | 12/1984 | Dancsi et al. | |
| 4,499,096 A | 2/1985 | Lotsof | |
| 4,558,053 A | 12/1985 | Rolski et al. | |
| 4,587,243 A | 5/1986 | Lotsof | |
| 4,596,676 A | 6/1986 | Cullinan | |
| 4,746,665 A | 5/1988 | Szantay | |
| 4,769,453 A | 9/1988 | Potier et al. | |
| 4,841,045 A | 6/1989 | Kuehne | |
| 4,897,477 A | 1/1990 | Kuehne | |
| 4,935,509 A | 6/1990 | Kuehne | |
| 4,946,833 A | 8/1990 | Lavielle et al. | |
| 5,095,109 A | 3/1992 | Kuehne | |
| 5,152,994 A | 10/1992 | Lotsof | |
| 5,369,111 A | 11/1994 | Kuehne et al. | |
| 5,654,281 A | 8/1997 | Mayer et al. | |
| 5,863,927 A | 1/1999 | Smith et al. | |
| 5,965,567 A | 10/1999 | Archer et al. | |
| 6,211,360 B1 | 4/2001 | Glick et al. | |
| 6,780,871 B2 | 8/2004 | Glick et al. | |
| 9,399,642 B2 | 7/2016 | Boulanger | |
| 9,399,643 B2 | 7/2016 | Boulanger | |
| 10,906,912 B2 | 2/2021 | Boulanger | |
| 11,827,643 B2 | 11/2023 | Boulanger | |
| 2009/0281134 A1 | 11/2009 | Glick et al. | |
| 2010/0152200 A1 | 6/2010 | Miller et al. | |
| 2013/0178618 A1 | 7/2013 | Boulanger | |

FOREIGN PATENT DOCUMENTS

| | | |
|---|---|---|
| WO | WO 00/38677 | 7/2000 |
| WO | WO 02/24700 | 3/2002 |

OTHER PUBLICATIONS

Bandarage. Tetrahedron, 1999, 55, 9405-24.
Bandarage. Current Medicinal Chemistry-Central Nervous System Agents, 2001, 1, 113-23.
Bornmann. Journal of Organic Chemistry, 1992, 57, 1752-60.
Greene. Protective Groups in Organic Synthesis, 1999, pp. 494-503 and 574-581.
Office Action for U.S. Appl. No. 13/346,815 dated Apr. 23, 2014.
Office Action for U.S. Appl. No. 13/346,815 dated Aug. 25, 2016.
Office Action for U.S. Appl. No. 13/346,815 dated Sep. 5, 2013.
Office Action for U.S. Appl. No. 13/346,815 dated Sep. 30, 2014.
Office Action for U.S. Appl. No. 14/228,303 dated Oct. 20, 2015.
Office Action for U.S. Appl. No. 14/228,316 dated Oct. 28, 2015.
Zheng, Tetrahedron Letters, 2005, 46(20), 3529-32.
Acheson. Heterocyclic Compounds, 1965, 2630-33.
Keuhne. Journal of Organic Chemistry, 1978, 43(19), 3705-10.
Keuhne. Journal of Organic Chemistry, 1996, 61, 6001-6008.
Silverman. The Organic Chemistry of Drug Design and Drug Action, 2004, pp. 25-34.
Decker. Archiv der Pharmazie, 2003, 46(20), 3529-32.

*Primary Examiner* — Douglas M Willis

(74) *Attorney, Agent, or Firm* — King & Partners, PLC

(57) ABSTRACT

Reactions, reagents and process conditions for the preparation of methyl 3-bromo-2-(2,3,4,9-tetrahydro-1h-pyrido[3,4-b]indol-1-yl)propanoate.

2 Claims, 6 Drawing Sheets

Scheme 1

Kuehne's Original Route to indole 1

Scheme 3

AMRI's Preparation of Aldehyde 6

Scheme 4

Improved Process to make 1

Scheme 5

New Route to Aldehyde 6

Scheme 6

Alternative New Route to Aldehyde 6

PROCESS FOR PREPARING METHYL 3-BROMO-2-(2,3,4,9-TETRAHYDRO-1H-PYRIDO[3,4-B]INDOL-1-YL)PROPANOATE

CROSS-REFERENCE TO RELATED APPLICATIONS

This application relates to U.S. application Ser. No. 17/136,103, filed Dec. 29, 2020, entitled "Novel Pharmaceutical Intermediates and Methods for Preparing the Same," which is hereby incorporated herein by reference in its entirety, including all references cited therein.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to novel pharmaceutical intermediates and to methods for efficiently preparing both indole and aldehyde derived pharmaceutical intermediates in the synthesis of 18-methoxycoronaridine (i.e., 18-MC, MM-110) and congeners and derivatives thereof.

2. Background Art

The original synthesis of 18-methoxycoronaridine and its congeners was devised to be convergent, with the combination of an independently prepared indole portion and an independently prepared aldehyde portion. Even in the early open literature, significant difficulties were reported from efforts to scale up the reported chemistry. The present invention discloses improvements to processes that allow for the efficient preparation of certain indoles and aldehydes, and consequently of 18-methoxycoronaridine itself. It also discloses new compounds resulting from these unique processes.

In particular, while the original description of the synthesis of indole 1 by Kuehne is adequate to produce research scale quantities of the requisite material, it is nonetheless problematic to produce significant quantities as is relevant for the full-scale production of, for example, an FDA approved drug (See FIG. 1; Scheme 1).

In accordance with Kuehne's original route, the classical conversion of tryptamine 2 to its free base 3 is straightforward, as is the production of methyl chloropyruvate from methylpyruvate via thionyl chloride. The Pictet-Spengler reaction of these two materials provides the corresponding intermediary product 4 in about a 70% yield. However, the ring expansion of intermediary product 4 to intermediary product 5 requires a very large proportion of expensive pyridine and produces a considerable quantity of undesirable tars. These tars are difficult to remove, and adversely impact the subsequent chemistry. Moreover, the sodium cyano borohydride reduction of intermediary product 5 to intermediate 1 is especially problematic, and Kuehne reports serious problems with decarbomethoxylation with increasing scale. The increasing side products make isolation of pure intermediate 1 essentially impossible.

Moreover, the classical aldehyde synthesis used by Kuehne is also replete with similar undesirable drawbacks and/or complications (See FIG. 2; Scheme 2).

It is therefore an object of the present invention to provide novel methods for efficiently preparing both indole and aldehyde derived pharmaceutical intermediates in the synthesis of 18-MC and congeners/derivatives thereof.

SUMMARY OF THE INVENTION

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

The present invention is directed to a pharmaceutical intermediate, comprising, consisting essentially of, and/or consisting of the structure:

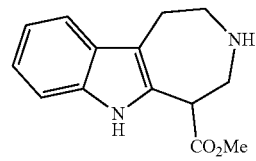 [SMILES: COC(=O)C1CNCCc2c1[nH]c1ccccc21]

wherein the pharmaceutical intermediate and any precursor intermediates are prepared in the absence of thionyl chloride.

The present invention is also directed to a reaction mixture to yield an indole pharmaceutical intermediate comprising, consisting essentially of, and/or consisting of:

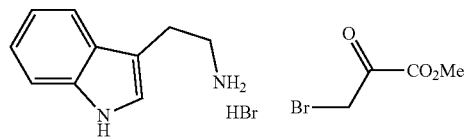 [SMILES: NCCc1c[nH]c2ccccc12 ; Br ; COC(=O)C(=O)CBr]

wherein the resulting indole pharmaceutical intermediate is

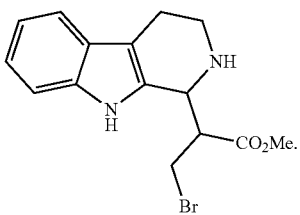 [SMILES: COC(=O)C(CBr)C1NCCc2c1[nH]c1ccccc21]

The present invention is further directed to a pharmaceutical intermediate, comprising, consisting essentially of, and/or consisting of the structure:

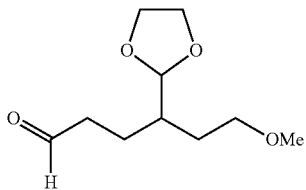 [SMILES: COCCC(CCC=O)C1OCCO1]

wherein the pharmaceutical intermediate and any precursor intermediates are void of

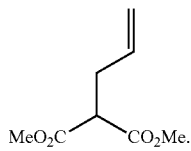

The present invention is yet further directed to a pharmaceutical intermediate, comprising, consisting essentially of, and/or consisting of the structure:

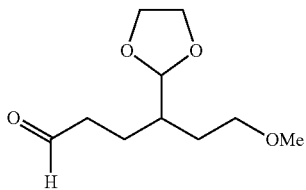 [SMILES: COCCC(CCC=O)C1OCCO1]

wherein the pharmaceutical intermediate and any precursor intermediates are void of an allyl containing compound.

The present invention is also directed to a pharmaceutical intermediate, comprising, consisting essentially of, and/or consisting of the structure:

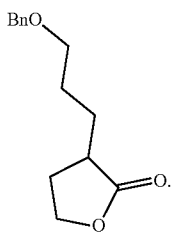

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted.

It will be further understood that the invention is not necessarily limited to the particular embodiments illustrated herein.

Figure 1:
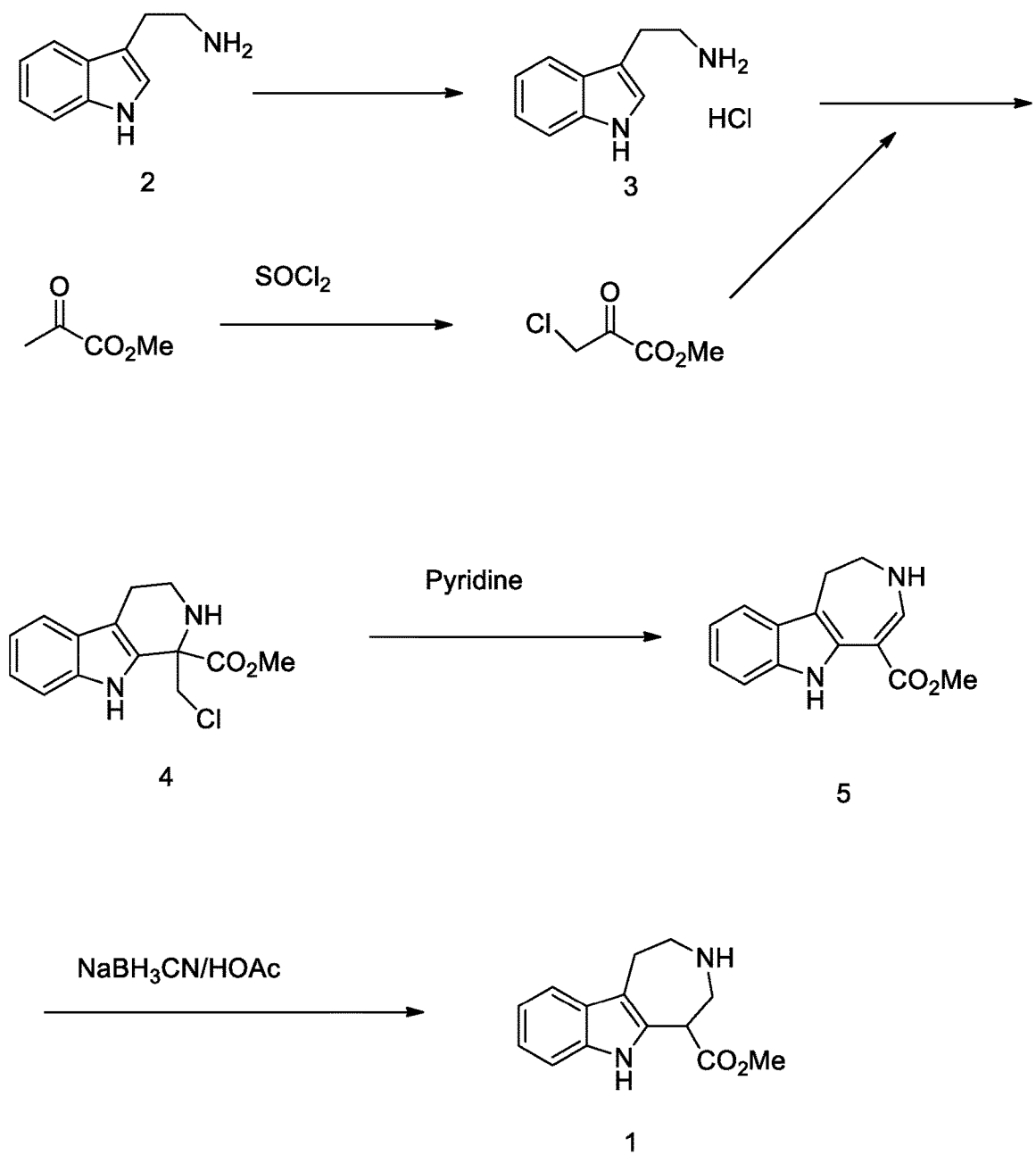
Figure 2:
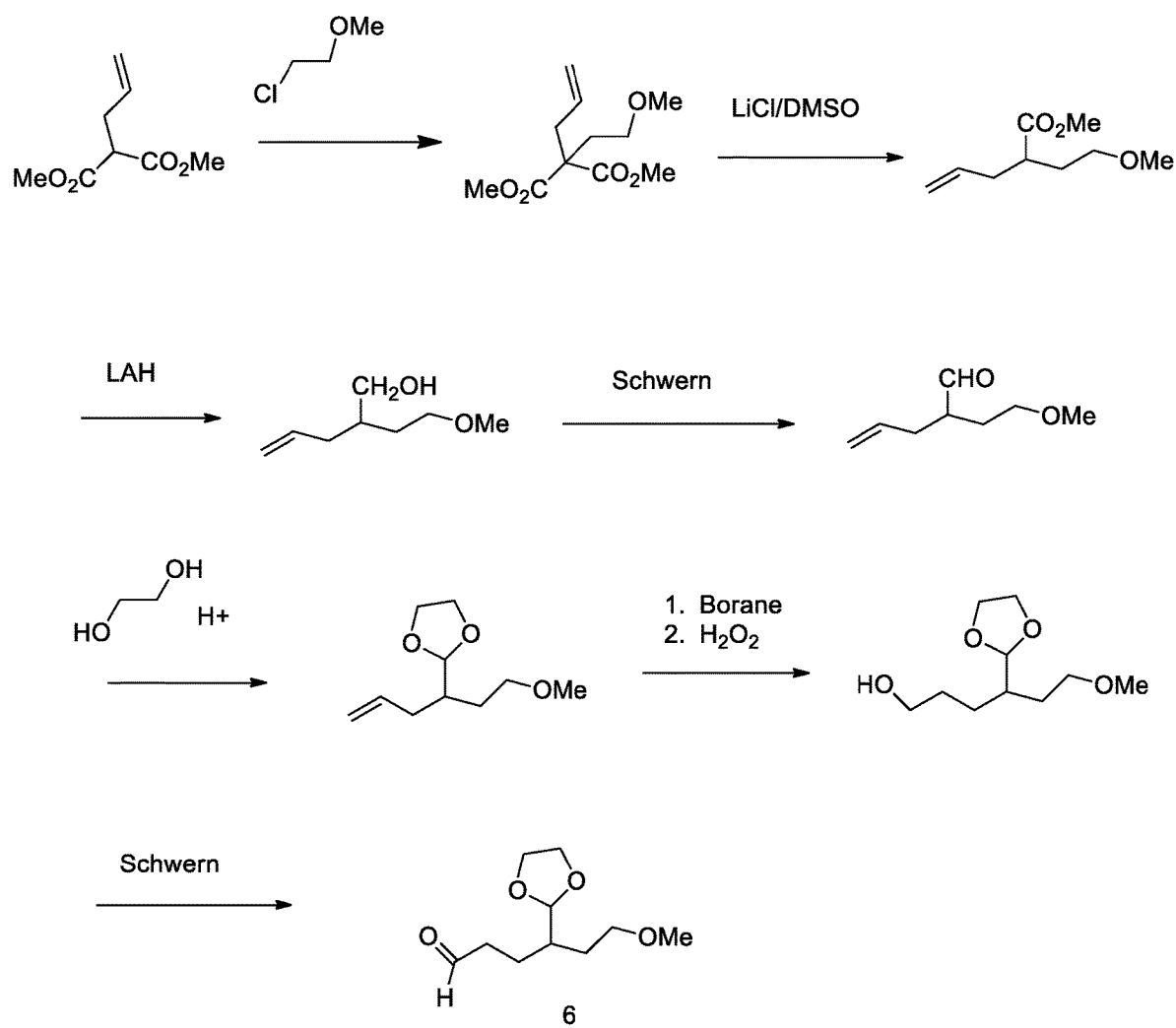
Figure 3:
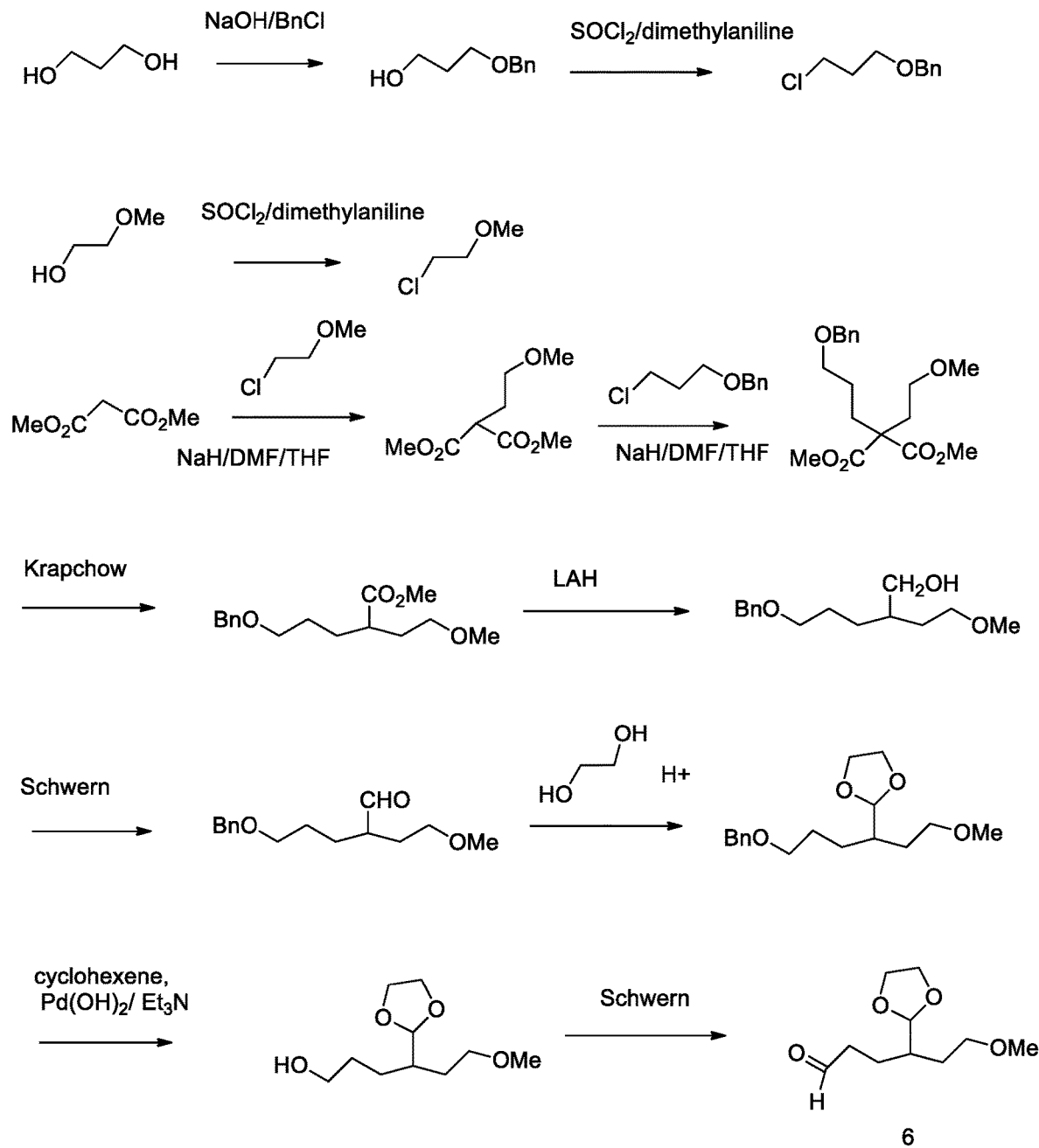
Figure 4:
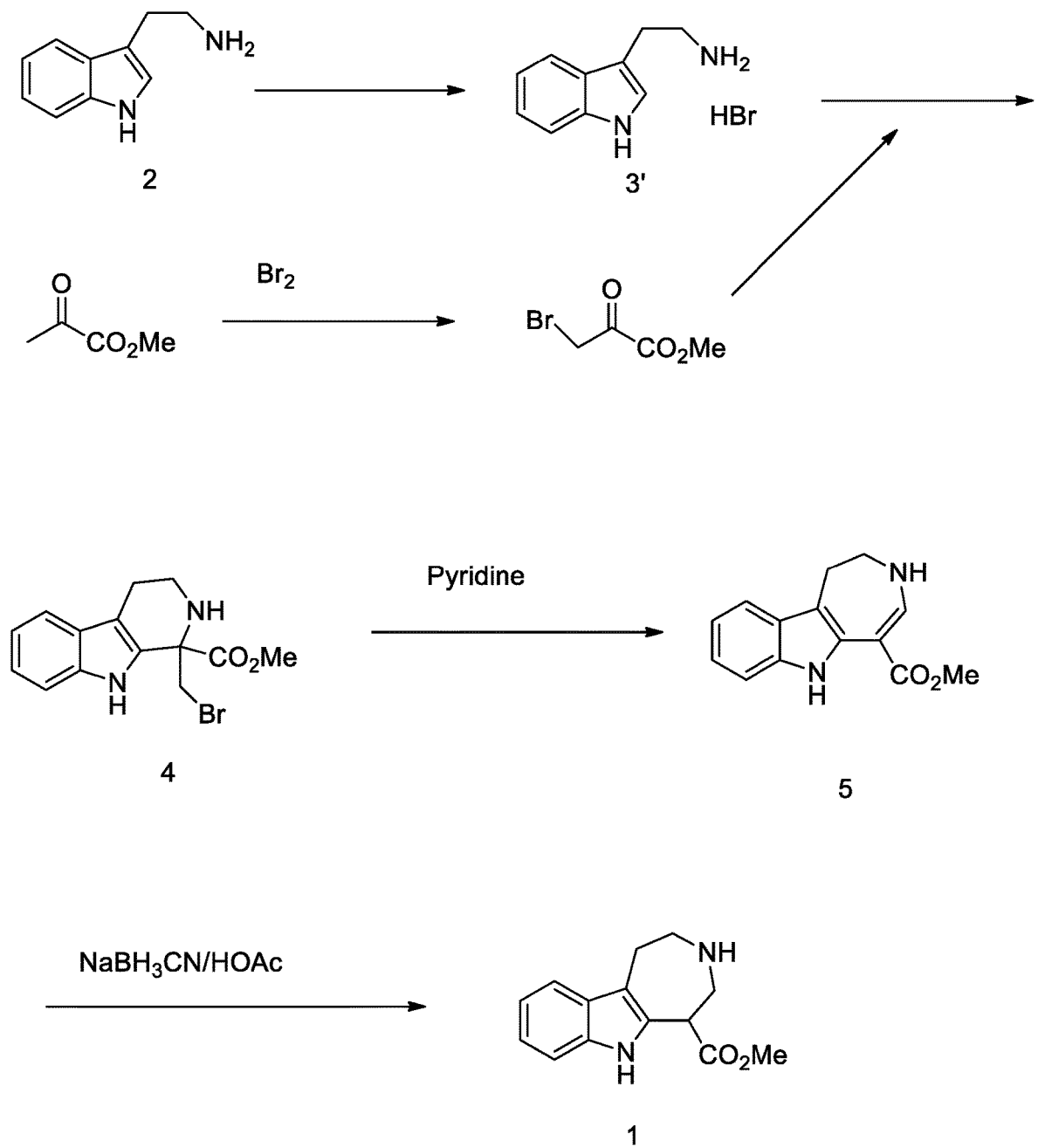
Figure 5:
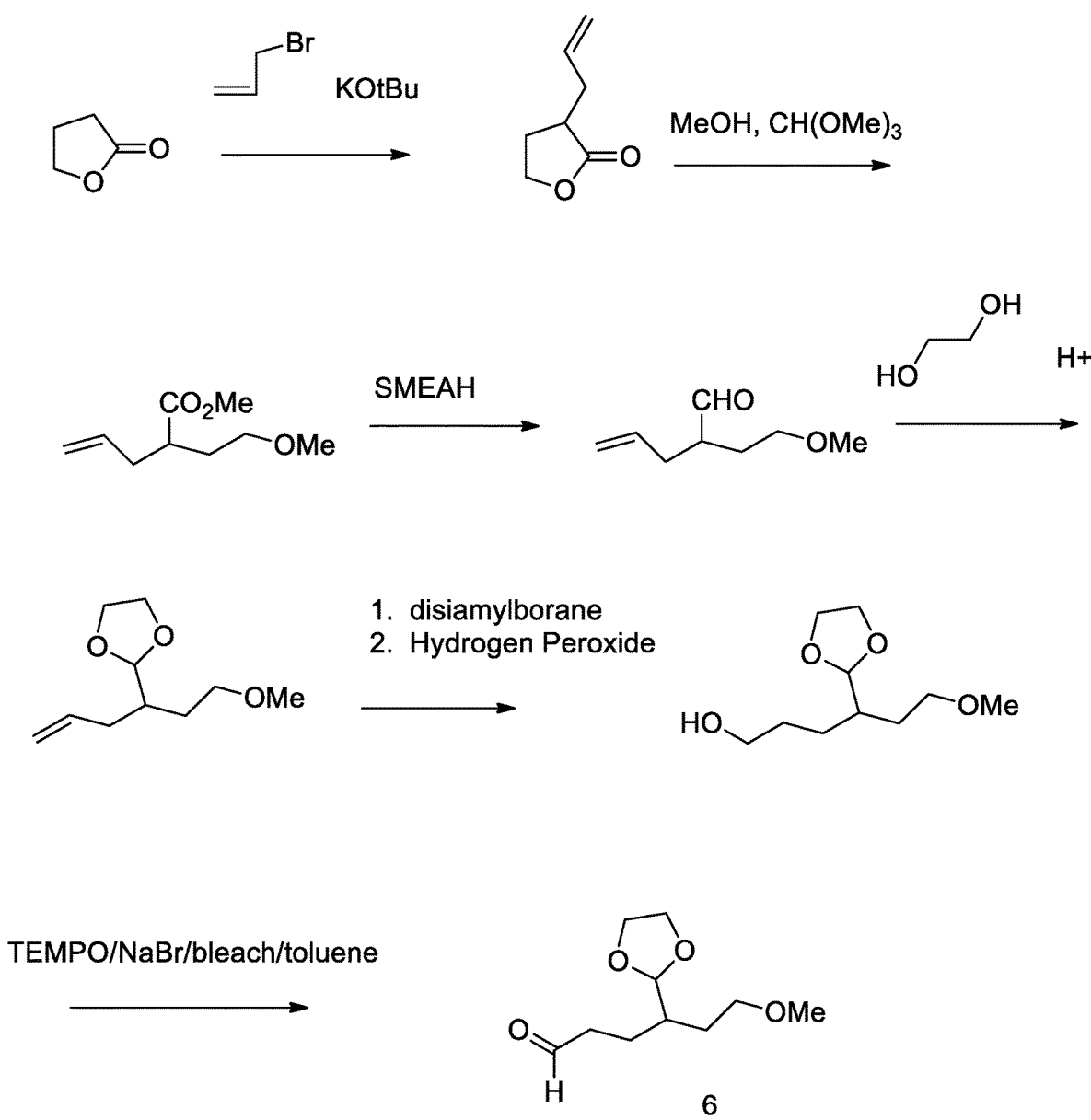
Figure 6:
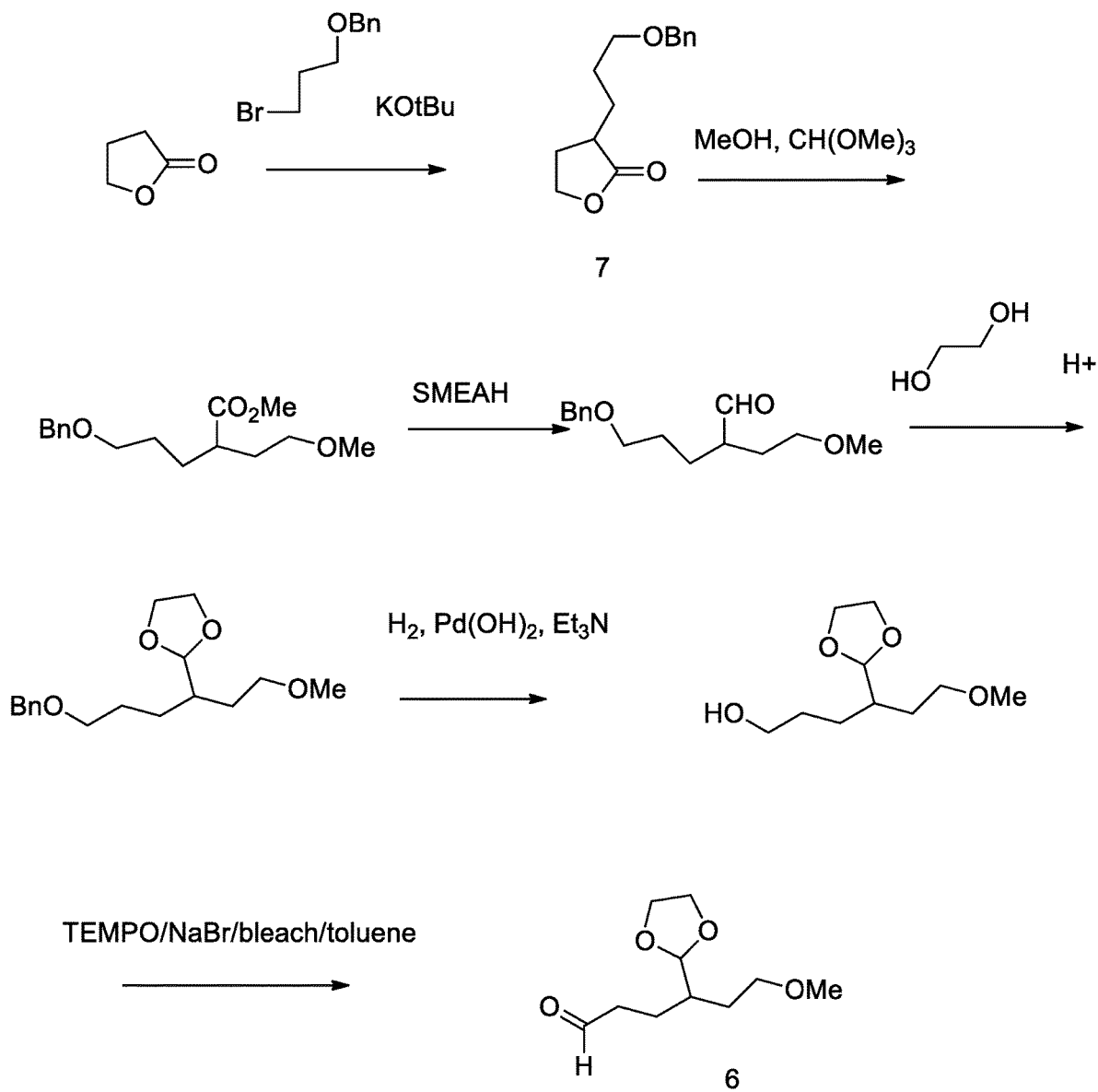

The invention will now be described with reference to the drawings wherein:

FIG. 1 of the drawings is a schematic flowchart for the synthesis of an indole pharmaceutical intermediate using Kuehne's classical route;

FIG. 2 of the drawings is a schematic flowchart for the synthesis of an aldehyde pharmaceutical intermediate using Kuehne's classical route;

FIG. 3 of the drawings is a schematic flowchart for the synthesis of an aldehyde pharmaceutical intermediate using AMRI's route;

FIG. 4 of the drawings is a schematic flowchart for the synthesis of an indole pharmaceutical intermediate using a route of the present invention;

FIG. 5 of the drawings is a schematic flowchart for the synthesis of an aldehyde pharmaceutical intermediate using a route of the present invention; and FIG. 6 of the drawings is a schematic flowchart for the synthesis of an aldehyde pharmaceutical intermediate using an alternative route of the present invention.

DETAILED DESCRIPTION OF THE INVENTION

While this invention is susceptible of embodiment in many different forms, there is shown in the structural formulas and described herein in detail several specific embodiments with the understanding that the present disclosure is to be considered as an exemplification of the principles of the invention and is not intended to limit the invention to the embodiments illustrated. It will be understood that the structural formulas disclosed herein are intended to comprise all stereochemical configurations regardless of graphical representations.

The present invention is directed to novel pharmaceutical intermediates and methods for efficiently preparing both indole and aldehyde derived pharmaceutical intermediates, preferably in the synthesis of 18-methoxycoronaridine (i.e., 18-MC, MM-110) and congeners and derivatives thereof.

Indole Intermediate

As was previously discussed hereinabove, Kuehne's original route to indole 1 (See FIG. 1) was replete with complications, including, among other things, not being applicable for large scale synthesis. However, the present invention provides for a novel route to indole 1 which overcomes the drawbacks and complications associated with Kuehne's original route (See FIG. 4).

As is shown in FIG. 4, the novel process starts with the conversion of free base tryptamine to its hydrobromide salt, best via HBr and an alcoholic solvent. Next methyl pyruvate is converted to the corresponding methyl bromopyruvate by use of bromine or copper (II) bromide. The Pictet Spengler of the hydrochloride salt of tryptamine and methyl bromopyruvate has been reported in the open literature, but this reaction suffered from considerable interference of the chloride, so that the resulting product was 80% bromide and 20% chloride. As the tars are associated with the chloride, this did not fully solve the problem of tar formation. However, by use of tryptamine hydrobromide, no salt exchange occurs, and the product is cleanly the hydrobromide. The hydrobromide cleanly ring-opens to 5 in at least an 80% yield, with minimal tar formation. This route removes the tar associated which is also produced by this reaction, but is impossible to remove after this step due to similarity to the properties of the next product. Therefore, this is a critical step if quality indole 1 is to be produced. Intermediate 5 is purified by dissolving in methylene chloride and treated with increments of silica gel, which is then removed by filtration. The presence of remaining tar is monitored by thin layer chromatography on silica gel using methylene chloride and visualizing with UV light. When removal is judged complete, the methylene chloride solution is concentrated to remove the solvent. Next, the residue is dissolved in 2 vol/wt hot acetone, followed addition of 0.8 vol/wt water. It is important to allow crystallization to occur around room temperature (20° C.), and not chill the solution, or impurities will be driven out of solution and coat/contaminate the purified product. The crystallized product may be recovered by filtration, and dried. If the product has a chocolate brown color, a poor quality 1 will ultimately be obtained. If it has a bright yellow color, pure product 1 will be obtained.

The reduction of intermediate 5 to product 1 may be achieved by borane, Adam's catalyst and hydrogen in glacial acetic acid, or most cost-effectively by sodium cyanoborohydride in glacial acetic acid. Regardless of method, the workup is critical to successful recovery of a good yield of good quality of product 1, much more so than the reaction itself. The reduction is best achieved at or about 20° C. in glacial acetic acid with methylene chloride co-solvent, with 1.6 equivalents of sodium cyanoborohydride divided into four equal parts added every 1.5 hrs. If the methylene chloride co-solvent is not used, the starting indole must be finely ground or the reaction will never reach completion. It is critical that the reaction be monitored by HPLC after the final addition, as even small amounts of unreacted starting material can't be subsequently removed. It is typical to allow the reaction to stir at 20° C. for 15 hours or more to achieve completion. If necessary, a small additional portion of sodium cyanoborohydride may be added if the reaction has not reached completion after 20 hrs.

Next, using a good vacuum and a pot temperature of no more than 50° C., approximately half of the glacial acetic acid is removed. Some water (approximately the same volume) is then added for dilution and transfer purposes. The next step will generate hydrogen cyanide gas, so adequate ventilation and scrubbing are required. 12 N hydrochloric acid is very slowly added until the reaction just shows a pH of approximately 1. This mixture is stirred for 1 hour at about 20° C. to destroy any remaining reagent. To remove tars, the mixture is extracted with a 1:1 mixture of toluene/ethyl acetate. Then an equal volume of ice is added, or of cold water, with the resulting mixture being cooled below 5° C. Then methylene chloride is added, followed by careful addition of an excess of ammonium hydroxide to pH 12, while keeping the internal temperature below 20° C. The pre-addition of methylene chloride serves to capture the free base as it is formed, rather than allow it to be exposed to a basic solution and degrade. The layers are separated, then the aqueous layer must be extracted once more with methylene chloride. The combined organic layers are dried over sodium sulfate, filtered, and the solvent removed in vacuo. The resulting crude product is recrystallized from ethyl acetate/hexanes to give white or off-white indole intermediate 1 in high purity and in yields 75% to 90%.

Advantageously, the route shown in FIG. 4 provides for the pharmaceutical intermediate, comprising the structure:

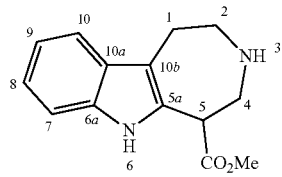

methyl 1,2,3,4,5,6-hexahydroazepino[4,5-b]indole-5-carboxylate wherein the pharmaceutical intermediate and any precursor intermediates are prepared in the absence of thionyl chloride.

Advantageously, the route shown in FIG. 4 also provides for a reaction mixture that yields an indole pharmaceutical intermediate, comprising:

(1) hydrogen bromide;

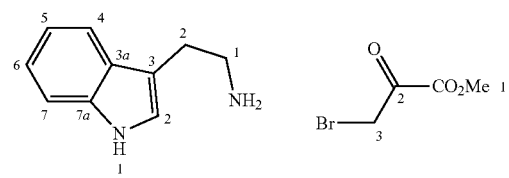 [SMILES: NCCc1c[nH]c2ccccc12 ; COC(=O)C(=O)CBr]

(2) 2-(1H-indol-3-yl)ethan-1-amine; and (3) methyl 3-bromo-2-oxopropanoate, wherein the resulting indole pharmaceutical intermediate is

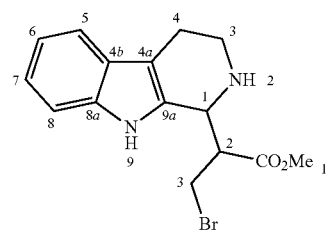 [SMILES: COC(=O)C(CBr)C1NCCc2c1[nH]c1ccccc21]

methyl 3-bromo-2-(2,3,4,9-tetrahydro-1H-pyrido[3,4-b]indol-1-yl)propanoate

Aldehyde Intermediate.

Although Kuehne's synthesis of the critical aldehyde component 6 made for a plausible bench preparation, it suffers from a number of serious issues that preclude its use for the production of full plant-scale synthesis. The first serious issue is that the route starts from dimethyl allylmalonate, a material that is not commercially available in bulk quantities. Furthermore, there are two Schwern-type oxidations that give significant sulfuraceous by-products, depleting the yield and contaminating the product, and requiring low-temperature reactions. The borane used to introduce the alcohol late in the sequence shows poor regioselectivity, and creates difficult-to-separate by-products. The aldehyde 6 is itself a very delicate material, consisting of one protected aldehyde in the presence of a free aldehyde. Significant losses occur with distillation, or most attempts to purify it. Finally, the preparation requires nine steps, including the preparation of the reagent in the first conversion.

An alternate approach reported by AMRI (See FIG. 3) suffers from many more steps, and the need for a Schwern-type oxidation twice in the sequence, but it does side-step the costly use of a borane to introduce the second alcohol by starting with a higher oxidation state benzyloxy protecting group. The AMRI group abandoned the route utilizing borane because of poor regioselectivity, and nearly impossible separation of the wrong isomeric product.

The present invention provides two alternative synthetic routes for preparing the aldehyde 6 intermediate which are shown schematically in FIGS. 5 and 6. These routes resolve a substantially majority of the issues associated with the prior art routes discussed supra.

In particular, in Scheme 5 (See FIG. 5), the starting material is inexpensive and readily available (i.e., butyrolactone). This is allylated with allylbromide, potassium tert-butoxide and tetrabutylammonium bromide in excellent yields. Next, in one reaction, the ring is opened to form the methyl ester and methyl ether by use of trimethylorthoformate and methanol, with an acid catalyst. The resulting product coincides with an intermediate in Kuehne's route, but is achieved much more efficiently. Next, rather than over-reduction to the alcohol, then re-oxidation to the aldehyde, the ester is directly reduced with Red-Al to the aldehyde. This is accomplished at reduced temperature in a batch reaction, or at room temperature using a flow reactor. The delicate aldehyde must be converted to the ethylene glycol acetal by classic Dean-Stark conditions, then distilled to purity under vacuum. The terminal alcohol may be installed with high regioselectivity by use of disiamyl borane, followed by oxidation with hydrogen peroxide. Care must be taken with the resulting alcohol, as it is sensitive to heat and acid. This precludes purification by distillation, so it is imperative that it is made as cleanly (e.g., contamination free) as possible. The final aldehyde 6 is very sensitive to heat and difficult to purify, so it is optimally made by a TEMPO oxidation in toluene or benzene, using just 1% TEMPO, catalytic sodium bromide, sodium bicarbonate buffer, and fresh sodium hypochlorite. The freshness of the sodium hypochlorite is critical to success, and a minimum used, approximately 1.3 eq. The reaction is optimally performed by maintaining the temperature between 0° C. and 5° C., and slowly metering in the reagent with a temperature-controlled metering pump. Higher temperatures or excess reagent result in losses of yield due to overoxidation to the acid. The product is very water-soluble, and then only aqueous phase contributed to the reaction is from the sodium hypochlorite (commercial bleach, approximately 5-8%). Workup involves separation of layers, drying over sodium sulfate, and removal of the solvent. This method leaves the TEMPO in the product, but it has proved to be an effective preservative. Also, some toluene is left in the product, even after aggressive removal in vacuo. Toluene is innocuous to the use of the aldehyde, and only requires a titer correction for use. Toluene, however, is very special to this reaction. Use of methylene chloride as is typical for TEMPO reactions gives a host of impurities, while a less polar solvent such as MTBE gives little reaction. Toluene gives the optimum and cleanest conversion.

As is best shown in FIG. 6, the present invention is directed to an alternative route to the aldehyde. It incorporates the prior art of AMRI's use of a higher oxidation state of the side chain to avoid the costly and problematic borane step. Using the same method as Scheme 5, butyrolactone may be alkylated with 3-benzyloxy-1-bromopropane. This can now be ring-opened to form the ether/ester with triethylorthoformate/methanol, reduced to the corresponding aldehyde with SMEAH, and made into the acetal with ethylene glycol under Dean-Stark conditions. It is optimally distilled to purity at this step, then deprotected using cyclohexene or hydrogen, palladium hydroxide, and triethylamine. TEMPO is once again employed to effect the final conversion to the corresponding aldehyde 6. In this sequence, compound 7 is new and has not been previously reported.

Compound 7 is provided below:

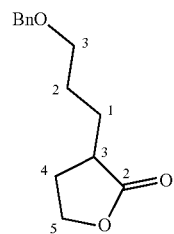

3-(3-(benzyloxy)propyl)dihydrofuran-2(3H)-one.

Advantageously, the route shown in FIG. 5 provides for the pharmaceutical intermediate, comprising the structure:

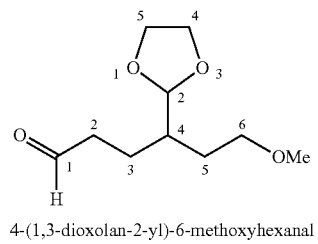 [SMILES: COCCC(CCC=O)C1OCCO1]

4-(1,3-dioxolan-2-yl)-6-methoxyhexanal wherein the pharmaceutical intermediate and any precursor intermediates are void of

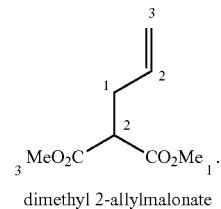

dimethyl 2-allylmalonate

It will be further understood that any reference to compounds disclosed herein includes pharmaceutically acceptable salts and/or solvates of the same.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

The invention claimed is:

1. A reaction mixture comprising:
(a) a compound of the following formula 3:

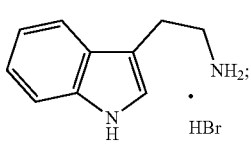

(b) a compound of the following formula:

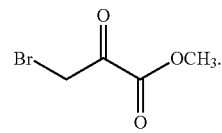

2. A process for preparing a compound of the following formula 4:

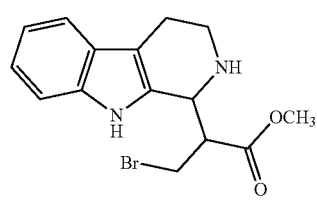

wherein the process comprises the following step:

reacting a compound of the following formula 3':

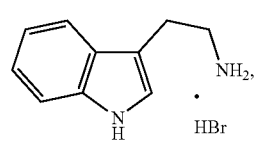

with a compound of the following formula:

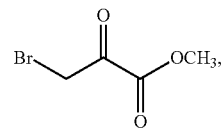

to provide a compound of the following formula 4:

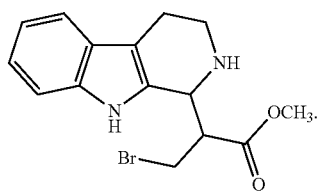

* * * * *